US 9,429,586 B2

(12) United States Patent
Watanabe et al.

(10) Patent No.: US 9,429,586 B2
(45) Date of Patent: Aug. 30, 2016

(54) AUTOMATIC ANALYZER

(75) Inventors: Atsushi Watanabe, Hitachinaka (JP);
Shigeki Matsubara, Hitachinaka (JP);
Kazuhiro Shimada, Hitachinaka (JP);
Kenji Teshigawara, Hitachinaka (JP);
Osamu Matsumoto, Mito (JP); Sylvia Rosenblatt, Benediktbeuren (DE);
Peter Wolf, Peissenberg (DE); Fridl Lang, Tutzing (DE); Roland Ihrig, Lampertheim (DE)

(73) Assignees: Hitachi High-Technologies Corporation, Tokyo (JP); Roche Diagnostics Operations Inc., Indianapolis, IN (US)

( * ) Notice: Subject to any disclaimer, the term of this patent is extended or adjusted under 35 U.S.C. 154(b) by 310 days.

(21) Appl. No.: 13/988,767
(22) PCT Filed: Nov. 28, 2011
(86) PCT No.: PCT/JP2011/077350
§ 371 (c)(1),
(2), (4) Date: Jul. 11, 2013
(87) PCT Pub. No.: WO2012/073878
PCT Pub. Date: Jun. 7, 2012

(65) Prior Publication Data
US 2013/0280129 A1 Oct. 24, 2013

(30) Foreign Application Priority Data
Nov. 29, 2010 (JP) .................... 2010-265492

(51) Int. Cl.
*G01N 35/10* (2006.01)
*G01N 35/00* (2006.01)
*G01N 35/04* (2006.01)

(52) U.S. Cl.
CPC .... *G01N 35/1002* (2013.01); *G01N 35/00663* (2013.01); *G01N 2035/00306* (2013.01); *G01N 2035/00673* (2013.01); *G01N 2035/0427* (2013.01)

(58) Field of Classification Search
CPC ............. G01N 2035/0462; G01N 2035/0465; G01N 2035/00673; G01N 35/00663
See application file for complete search history.

(56) References Cited

U.S. PATENT DOCUMENTS

| 7,749,441 B2 | 7/2010 | Hanawa et al. | |
| 2004/0253146 A1* | 12/2004 | Shiba et al. | ................... 422/64 |
| 2007/0255756 A1* | 11/2007 | Satomura et al. | ......... 707/104.1 |
| 2010/0001854 A1 | 1/2010 | Kojima | |

FOREIGN PATENT DOCUMENTS

| CN | 1576849 A | 2/2005 |
| CN | 101632024 A | 1/2010 |

(Continued)

OTHER PUBLICATIONS

Chinese Office Action received in Chinese Application No. 201180057309.9 dated Jan. 13, 2014.

*Primary Examiner* — Jill Warden
*Assistant Examiner* — Julie Tavares
(74) *Attorney, Agent, or Firm* — Mattingly & Malur, PC

(57) ABSTRACT

An automatic analyzer includes: first reagent storing means for storing a plurality of the reagent containers; second reagent storing means for storing a replacement reagent container in addition to the first reagent storing means; transfer means for transferring the reagent container from the second reagent storing means to the first reagent means; and a storing portion for storing the reagent container discharged from the second reagent storing means. The automatic analyzer includes control means for exercising control such that the information write means writes reagent information on the information recording medium immediately before the reagent container is transferred from the second reagent storing means to the first reagent storing means or immediately before the reagent container is discharged from the second reagent storing means to the storing portion.

12 Claims, 3 Drawing Sheets

(56) References Cited

FOREIGN PATENT DOCUMENTS

| JP | 2000-310643 A | 11/2000 |
| JP | 2005-37171 A | 2/2005 |
| JP | 3127156 U | 11/2006 |
| JP | 2009068992 A | 4/2009 |
| JP | 2009-270841 A | 11/2009 |
| JP | 4697140 B2 | 3/2011 |
| WO | 2006/009251 A1 | 1/2006 |

* cited by examiner

AUTOMATIC ANALYZER

TECHNICAL FIELD

The present invention relates to an automatic analyzer analyzing a biological sample such as blood, urine or the like. In particular, the invention relates to an automatic analyzer provided with means for automatically replacing a reagent container and to an assistance technique in the automatic analyzer.

BACKGROUND ART

Automatic analyzers that perform qualitative and quantitative analysis on biological samples such as blood, urine and the like are increased in the reagent consumption rate and in the frequency of replacing reagent containers, along with the increased number of samples to be processed and increased measurement items. On the other hand, it is required to reduce operator's work as much as possible in order to reduce cost such as manpower expense. Thus, it is desired to simplify work for replacing a reagent container.

Also the sample processing speed of the automatic analyzer is largely increased. Therefore, reagent replacing work desires to minimize the interruption of analyzing operation without bringing the operation of the analyzer to a halt.

For example, in patent document 1, a second reagent storing means for replacement is installed in addition to a first reagent storing means located in an analyzing unit. Further, a reagent transfer means is installed between the second reagent storing means for replacement and the first reagent storing means in the analyzing unit. In this way, it is intended to simplify reagent replacing work and to minimize the interruption of analyzing work.

In patent document 2, an analysis system includes an analysis apparatus using a reagent container having a memory storing reagent information concerning the reagent in the container and a remote computer. The analysis system executes a step for reading reagent information from the memory of the reagent container, a step for judging whether the usage of the reagent in the reagent container is inhibited or not on the basis of the reagent information, a step for writing the usage inhibition data into the memory of the reagent container when the usage of the reagent in the reagent container is inhibited, and a step for registering the usage inhibition data corresponding to the ID of the reagent container into a reagent DB controlled by the remote computer when the usage of the reagent in the reagent container is inhibited.

PRIOR-ART DOCUMENT

Patent Document
Patent Document 1
  JP-A-2005-37171
Patent Document 2
  JP-A-2006-529296

SUMMARY OF THE INVENTION

Problem to be Solved by the Invention

In patent document 1 mentioned above, in the automatic analyzer provided with the second reagent storing means for replacement having no cold storage function in addition to the conventional first reagent storing means having a cold storage function, there is concern that a reagent degrades as the elapsed time while the reagent container is placed in the second reagent storing means for replacement is long. Therefore, there is a need for a higher level of reagent management than that of the conventional storing means having a cold storage function. A first problem to be solved by the present invention is to realize reagent management more reliable than that of a conventional reagent storing means having a cold storage function in an automatic analyzer provided with replacement reagent storing means especially having no cold storage function.

In patent document 2 mentioned above, the Information written into the memory of the reagent container is the reagent information of the usage inhibition. On the other hand, a regent container can be used in apparatuses of same kinds of apparatuses, being used in the kind of apparatus, so that reagent information, such as an elapsed time after opening of a reagent of the like, continuously used become effective reagent information in an automatic analyzer in which the reagent container is used. Therefore, another problem to be solved by the present invention is to provide an automatic analyzer writing the information of the reagent continuously used, especially in the reagent information controlled by the automatic analyzer into the information recording medium included in a reagent container.

Means for Solving the Problem

The present invention is characterized by, in an automatic analyzer that dispenses a sample to be analyzed and a reagent used for the analysis and mixes the liquids thus dispensed together to react with each other for analysis, including an information recording medium for recording reagent information provided on a reagent container; information reading means for reading the reagent information from the information recording medium; information writing means for recording the reagent information in the information recording medium; first reagent storing means for storing the reagent container; second reagent storing means for storing a replacement reagent container in addition to the first reagent storing means; transfer means for transferring the reagent container from the second reagent storing means for replacement to the first reagent storing means; and information writing means provided in at least one of the first reagent storing means, the second reagent storing means and the transfer means, and in that the reagent information is written on the information recording medium by the information writing means.

Effect of the Invention

The present invention can provide the automatic analyzer that realizes reagent management with a high degree of reliability, reduces an operator's burden due to work such as reagent replacement or the like, and minimizes the interruption of analysis operation without the occurrence of reagent shortage during the analysis.

The reagent management using, particularly, continuously usable reagent information among the reagent information managed on the automatic analyzer is realized to perform the reagent management of a higher order. Thus, the saving of the reagent and sample is achieved and further the lowering of analysis accuracy due to abnormality can be reduced.

The present invention can reduce an operator's work burden such as re-measurement due to the degradation of the reagent.

MODE FOR CARRYING OUT THE INVENTION

Figure 1:
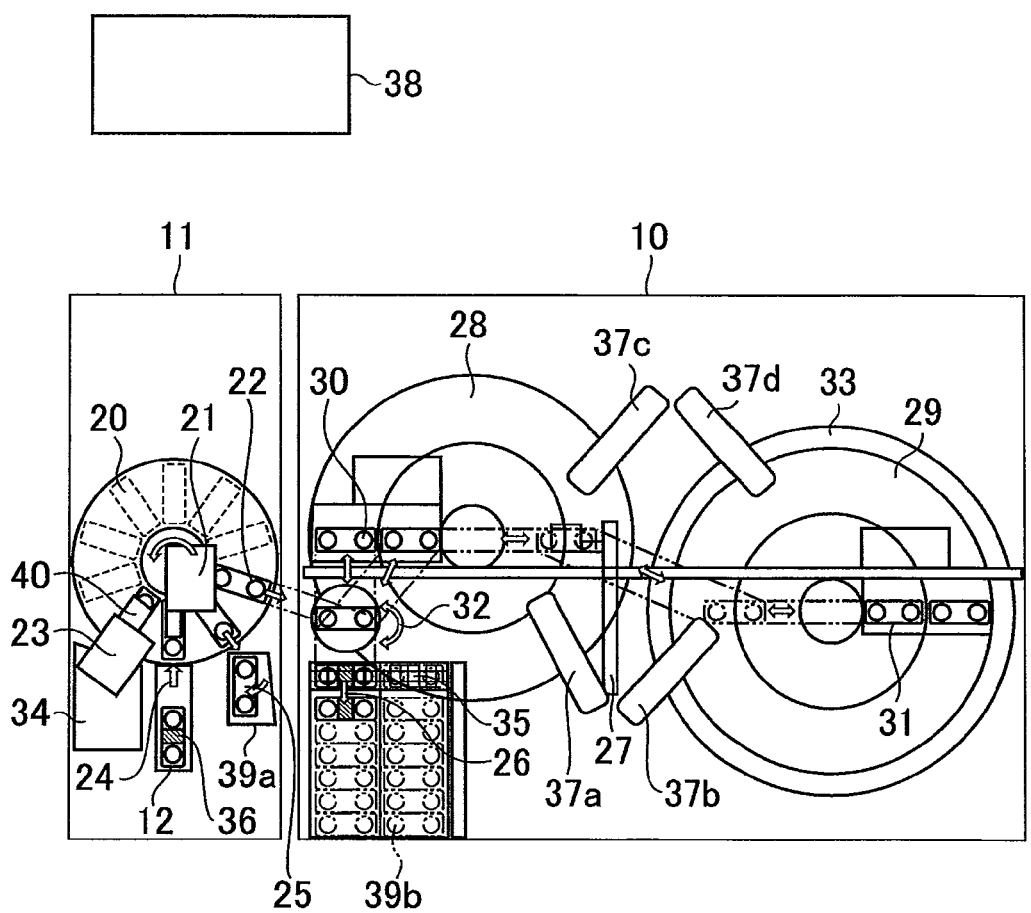
FIG. 1 is a plan view of an automatic analyzer according to the present invention.

A basic configuration of embodiments of the present invention will hereinafter be described in detail with reference to the drawings. FIG. 1 is a plan view of an automatic analyzer.

The automatic analyzer is composed of an analyzing unit 10 and a buffer unit 11. The analyzing unit 10 includes a reagent depository 28; a reagent depository 29; a reagent dispensing mechanism 37; fluid volume detecting means provided in the reagent dispensing mechanism 37 similarly; a reagent transfer mechanism 27 for transferring a reagent container 12 having been transferred from the buffer unit 11 side, to the reagent depository 28 or 29; a reagent discharge-storage mechanism 26 which discharges the reagent container 12 from the analyzing unit 10; and a reagent read/write mechanism 35 which reads and writes reagent information. The buffer unit 11 includes a replenishment reagent depository 20 which temporarily holds a replenish reagent; liquid volume detecting means installed in the replenishment reagent depository 20; a reagent information read/write mechanism 21 which reads and writes reagent information; and a reagent discharge mechanism 25 which discharges a reagent container from the buffer unit 11. A description is given of a procedure for transferring the reagent container 12 by use of this apparatus.

An operator first puts a reagent container 12 at a port provided in the reagent replenishment mechanism 24. The reagent container 12 is transferred to the replenishment reagent depository 20 by the reagent replenishing mechanism 24. An information recording medium 36, an RFID tag for example, in which information such as a reagent residual quantity, a lot, an expiration date, etc. are recorded is attached to the reagent container 12 having been transferred to the replenishment reagent depository 20. Such information is read by the reagent information read/write mechanism 21 installed on the upper side of the replenishment reagent depository 20 and is stored in a control computer 38.

In this case, when the control computer determines that a certain reagent container 12 is unusable for analysis because the reagent information on the reagent container 12 cannot be read, such a reagent container 12 is discharged by the reagent discharge mechanism 25 provided in the buffer unit 11.

When it is requested that a reagent need be replenished for a container, the reagent is transferred to a cap opening position of a reagent cap opening mechanism 23 within the replenishment reagent depository 20 on which reagents have previously been mounted. A reagent cap of the reagent container 12 is then opened at the cap opening position and is discarded into a reagent cap discard box 34.

The reagent container 12 whose reagent cap has been opened is measured in fluid volume by the fluid volume detecting means installed in the replenishment reagent depository 20. The fluid volume thus measured is stored in a control computer 38. The reagent container 12 subjected to fluid volume measurement is transferred to the reagent container delivery position in the replenishment reagent depository 20. The reagent container 12 is then transferred to the analyzing unit 10 by the reagent container transfer mechanism 22.

Incidentally, if the timing of reagent replacement is within a range where reagent shortage does not occur, the reagent replacement is performed using a vacant cycle between sample transfers or time between first regent dispensing and second reagent dispensing. If the reagent replacement is not made in time by any means, specimen sampling is interrupted and a reagent container is placed after the reagent is dispensed into the specimen prior to the interruption. In any of these cases, the state of the analyzer is under analysis. In other words, the analyzer is not temporarily stopped to replenish the reagent. Therefore, the time of the analysis interruption can be shortened.

The reagent container 12 (hereinafter, described to reagent bottle) transferred to the analyzing unit 10 is set in a reagent turning mechanism 32 installed in the analyzing unit 10. The reagent turning mechanism 32 turns the reagent bottle 12 in the direction in which to mount the reagent cassette 12 onto the reagent depository 28 or 29. The reagent bottle 12 whose direction has been changed is transferred by the reagent transfer mechanism 27 to one of the reagent depositories 28 and 29 that has been requested to replace the reagent.

After having transferred the reagent container 12 to the reagent depository 28 or 29, the reagent transfer mechanism 27 transfers a reagent container 12 to be replaced because of a small residual amount of reagent, from the reagent depository 28 or 29 to the reagent discharge-storage mechanism 26. The reagent discharge-storage mechanism 26 transfers the reagent container 12 to a storing portion 39b in the reagent discharge-storage mechanism 26. In addition, the reagent container 12 is stored thereat until it will be picked out by an operator.

Figure 2:
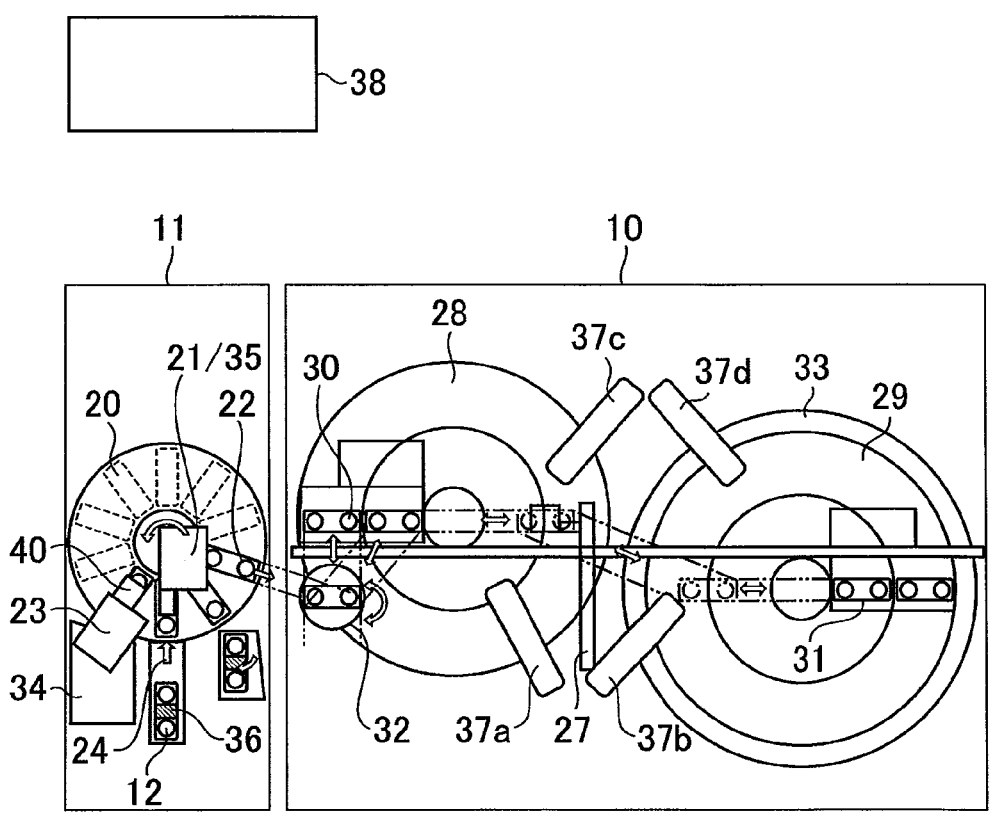
FIG. 2 is a plan view of an automatic analyzer according to the present invention by way of another example.
Figure 3:
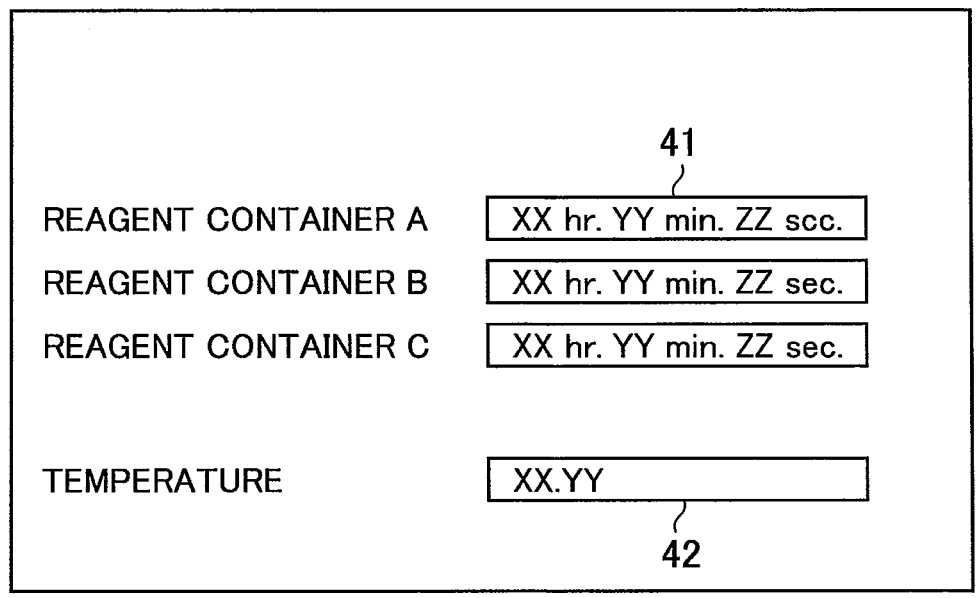
FIG. 3 is a detail plan view of a screen for the control computer on an automatic analyzer according to the present invention.

Another embodiment of the present invention is described in detail by use of FIG. 2.

FIG. 2 is a plan view of an automatic analyzer according to another embodiment.

The automatic analyzer is composed of an analyzing unit 10 and a buffer unit 11. The analyzing unit 10 includes a reagent depository 28; a reagent depository 29; fluid volume detecting means provided in a reagent dispensing mechanism 37; and a reagent transfer mechanism 27 for transferring a reagent container 12 having been transferred from the buffer unit 11 side, to the reagent depository 28 or 29. The buffer unit 11 includes a replenishment reagent depository 20 which temporarily holds replenish reagent; liquid volume detecting means installed in the replenishment reagent depository 20; a reagent information read/write mechanism 35 which reads and writes reagent information; and a reagent discharge mechanism 25 which discharges a reagent container. A description is given of a procedure for transferring the reagent container 12 by use of this apparatus.

An operator first puts a reagent container 12 at a port provided in the reagent replenishment mechanism 24. The reagent container 12 is transferred to the replenishment reagent depository 20 by the reagent replenishing mechanism 24. A RFID tag in which information such as a reagent residual quantity, a lot, an expiration date, etc. are recorded is attached to the reagent container 12 having been transferred to the replenishment reagent depository 20. Such information is read by the reagent information read/write mechanism 21 installed on the upper side of the replenishment reagent depository 20 and is stored in a control computer 38.

When it is requested that a reagent need be replenished for a container, the reagent is transferred to a cap opening position of a reagent cap opening mechanism 23 within the replenishment reagent depository 20 on which reagents have previously been mounted. A reagent cap of the reagent container 12 is then opened at the cap opening position and is discarded into a reagent cap discard box 34.

The reagent container 12 whose reagent cap has been opened is measured in fluid volume by the fluid volume detecting means installed in the replenishment reagent depository 20. The fluid volume thus measured is stored in a control computer. The reagent container 12 subjected to fluid volume measurement is transferred to the reagent container delivery position in the replenishment reagent depository 20. The reagent container 12 is then transferred to the analyzing unit 10 by the reagent container transfer mechanism 22.

Incidentally, if the timing of reagent replacement is within a range where reagent shortage does not occur, the reagent replacement is performed using a vacant cycle between sample transfers or time between first regent dispensing and second reagent dispensing. If the reagent replacement is not made in time by any means, specimen sampling is interrupted and a reagent container is placed after the reagent is dispensed into the specimen prior to the interruption. In any of these cases, the state of the analyzer is under analysis. In other words, the analyzer is not temporarily stopped to replenish the reagent. Therefore, the time of the analysis interruption can be shortened.

The reagent container 12 transferred to the analyzing unit 10 is set in a reagent turning mechanism 32 installed in the analyzing unit 10. The reagent turning mechanism 32 turns the reagent container 12 in the direction in which to mount the reagent container 12 onto the reagent depository 28 or 29.

The reagent container 12 whose direction has been changed is transferred by the reagent transfer mechanism 27 to one of the reagent depositories 28 and 29 that has been requested to replace the reagent. After having transferred the reagent container 12 to the reagent depository 28 or 29, the reagent transfer mechanism 27 transfers a reagent container 12 to be replaced because of a small residual amount of reagent, from the reagent depository 28 or 29 to the buffer unit 11 via the reagent turning mechanism 32 and the reagent container transfer mechanism 22. Such a reagent container 12 is then discharged to the reagent discharge mechanism 25. The reagent discharge mechanism 25 discharges the reagent container 12 to the storing portion in the reagent discharge mechanism 25. In addition, the reagent container 12 is stored thereat until it will be picked out by an operator.

Next, reagent information written on a RFID attached to a reagent container according to the present invention is described along a transfer route of the reagent container in the embodiment with FIG. 1. A description is given of writing reagent information in a discharge route from the buffer unit 11 and from the analysis unit 10. The reagent information written on the RFID in the discharge route from the buffer unit 11 is first described in detail.

An operator first puts a reagent container 12 at a port provided in the reagent replenishment mechanism 24. The reagent container 12 is transferred to the replenishment reagent depository 20 by the reagent replenishing mechanism 24. A RFID tag in which information such as a kind of the reagent, a reagent residual quantity, a lot, an expiration date, etc. are recorded is attached to the reagent container 12 having been transferred to the replenishment reagent depository 20. Such information is read by the reagent information read/write mechanism 21 installed on the upper side of the replenishment reagent depository 20 and is stored in a control computer 38.

The control computer 38 stores reagent information to be managed on the automatic analyzer during the time until the reagent container 12 is transferred into the analyzing unit 10 after the reagent container 12 is transferred into the replenishment reagent depository 20. Such reagent information includes the elapsed time of the reagent container placed in the replenishment reagent depository 20 and its permissible limit value, temperature in the replenishment reagent depository 20 and its permissible limit value, history of opening the cap of the reagent container 12, a combination of reagent containers, fluid volume of the reagent container, and the number of analysis. The reagent information is hereinafter described individually.

The control computer stores, as the reagent information to be written on the RFID, the placing elapsed time until the reagent container 12 is transferred into the analysis unit 10 after it is transferred into the replenishment reagent depository 20. Measurement start time for the placing elapsed time is the point of time when the RFID tag attached to the reagent container 12 is read in the reagent information read/write mechanism 21. It is desirable that measurement of the placing elapsed time be started from the point of time when the reagent container 12 is placed at the reagent charging port of the reagent replenishment mechanism 24. The elapsed time 41 can be measured by the control computer which may be equipped a clock function. The reagent information written on the RFID may be not the placing elapsed time but permissible limit residual time obtained by subtracting placing elapsed time from a set placing elapsed time permissible limit value.

The automatic analyzer is provided with a temperature sensor in the replenishment reagent depository 20. Temperature in the replenishment reagent depository 20 is stored in the control computer as another piece of reagent information written on the RFID. Temperature in the replenishment reagent depository 20 is constantly measured in the state where the automatic analyzer operates. The target reagent container starts to be measured from the point of time when the RFID tag attached to the reagent container 12 is read by the reagent information read/write mechanism 21. However, similarly to the placing elapsed time, it is desired that the measurement be started from the point of time when the reagent container 12 is placed at the reagent charging port of the reagent replenishment mechanism 24. The temperature 42 can be measured by the sensor which is equipped in the replenishment reagent depository 20.

The placing elapsed time and the temperature in the replenishment reagent depository 20 are detailed later.

If reagent replenishment is next requested, a reagent container 12 is transferred to a cap opening position of the reagent cap opening mechanism 23 in the replenishment reagent depository 20. The reagent container 12, which has reagent cap opened, is transferred to the analyzing unit 10 by the reagent transfer mechanism 22.

The reagent cap opening mechanism 23 is provided with a reagent cap detecting mechanism 40. If the reagent cap detecting mechanism 40 determines that a cap is attached, the reagent cap of the reagent container 12 is opened by the reagent cap opening mechanism 23 and is discarded into the reagent cap discard box 34.

The automatic analyzer stores the detection result of the reagent cap and the cap-opening history of the reagent container 12 as other pieces of reagent information written on the RFID into the control computer 38. The cap-opening history of the reagent container 12 includes data as to whether or not the cap is successfully opened by the reagent cap opening mechanism 23.

The automatic analyzer determines a combination of reagent containers, as another piece of reagent information written on the RFID, on the basis of the kind of the reagent, an expiration date, etc. included in the information read by the reagent information read/write mechanism 21. The combination of reagent containers is reagent information relating to an analysis item for which analysis is performed by use of reagents put in a plurality of corresponding reagent containers 12. This information is used as a combination of reagent containers used in calibration measurement inevitably performed before measurement or in actual measurement.

For example, an operator may transfer, to the automatic analyzer, a reagent container having a history indicating that the reagent container was used by another automatic analyzer. In such a case, the operator has an intended combination of reagent containers determined beforehand. Therefore, it is necessary to write data on the combination of the reagent containers used by another automatic analyzer on the RFID tag attached to the reagent container 12 so that the automatic analyzer can identify this combination of the reagent containers used by another automatic analyzer. For also a reagent container having a history indicating that the reagent container is not used, i.e., an unopened reagent container, it is necessary to determine the combination of the reagent containers to be used for analysis before the start of the analysis so that the automatic analyzer can identify the combination.

There may be a combination of reagent containers in a plurality of reagent containers 12 transferred into the replenishment reagent depository 20. In such a case, when appropriate reagent containers 12 are transferred from the buffer unit 11 to the analysis unit 10, they are transferred to one and the same reagent depository 28 or 29.

Therefore, the automatic analyzer includes means that determines a combination of reagent containers usable for analysis based on the information read by the reagent information read/write mechanism 21 after the reagent container 12 is transferred into the replenishment reagent depository 20 by the reagent replenishment mechanism 24. The combination of the reagent containers is stored in the control computer 38.

The automatic analyzer allows the fluid volume detecting means installed in the replenishment reagent depository 20 to measure the fluid volume of the reagent container as another piece of reagent information written on the RFID. The fluid volume of the reagent container is stored in the control computer 38.

The control computer 38 includes means for calculating how many analyses are executable by use of the fluid volume in the appropriate reagent container. The number of analysis executable is stored as reagent information relating to the fluid volume in the control computer 38.

The fluid volume of the reagent container and the number of analysis per reagent container correspond to reagent information written when the reagent container is transferred from the buffer unit 11 or also when the reagent container is transferred from the analyzing unit 10. The fluid volume of the reagent container and the number of analysis per reagent container is detailed later.

These reagent information are written on the reagent information write/read mechanism 21 arranged on the upper side of the replenishment reagent depository 20. The time at which to write the reagent information is immediately before the reagent container 12 is transferred from the replenishment reagent depository 20 to the analyzing unit 10 or to the storing portion 39a installed on the reagent discharge mechanism 25.

As mentioned before the reagent information written on the RFID tag attached to the reagent container 12, a detailed description is next given of the placing elapsed time and the temperature within the replenishment reagent depository 20.

If the RFID read information on the reagent container 12 is such that data on the placing elapsed time in the replenishment reagent depository 20 includes a previous value, accumulation (the sum of the previous value and a current value) of the placing elapsed time is stored in the control computer. The previous value includes not only an initial value having no write history but also a value written by the reagent information read/write mechanism 21. If the placing elapsed time is written on the RFID tag, the initial value of the placing elapsed time in the replenishment reagent depository 20 is updated.

The reagent information relating to the placing elapsed time includes the time when the reagent container 12 is transferred into the replenishment reagent depository 20 and the time at which the placing elapsed time exceeds the permissible limit value. Similarly, the reagent information relating to temperature in the replenishment reagent depository 20 includes the permissible limit value of the temperature.

The automatic analyzer has the permissible limit value of the placing elapsed time, and the time at which the placing elapsed time exceeds the permissible limit value is stored in the control computer 38.

Similarly to the expiration date of a reagent in a cold storage state, the permissible limit value of the placing elapsed time is set as an initial value for each analysis item. Depending on an analysis item, the permissible limit value may be set by the hour at a numerical value from 0 to 24 or by the minute at a numerical value from 0 to 1440.

The permissible limit value of the placing elapsed time is set as an initial value. However, taking environmental conditions, seasonal conditions and other conditions in each of facilities into consideration, the operator may edit the placing permissible limit value of the reagent information on a display screen or the like for higher order reagent management in conformity of the respective environmental conditions or operator's reagent management consciousness.

If the permissible limit value of the temperature is stored in the RFID tag, the automatic analyzer compares the temperature in the replenishment reagent depository 20 with the permissible limit value of temperature taking, as a starting point, the point of time when the RFID tag is read out by the reagent information read/write mechanism 21.

In contrast, if the automatic analyzer stores the permissible limit value of the temperature, it compares the temperature in the replenishment reagent depository 20 with the permissible limit value of temperature taking, as a starting point, the time when the reagent container 12 is transferred into the replenishment reagent depository 20. The comparison of temperature may be started from the point of time when the RFID tag is read.

The automatic analyzer stores, as reagent information relating to the permissible limit value of temperature, the placing elapsed time during a period of temperature abnormality in the range of from a starting point, i.e., the time when the temperature in the replenishment reagent depository 20 exceeds the permissible limit value to a terminating point, i.e., the time when the temperature becomes a value less than the permissible limit value. The accumulation of the placing elapsed time during the temperature abnormality period is stored in the control computer 38.

If the RFID read information on the reagent container includes a previous value of the placing elapsed time during the temperature abnormality period, the accumulation (the sum of the previous value and a current value) is written. The previous value includes not only an initial value having no write history but also a value written by the reagent information read/write mechanism 21. If the previous value is written by the reagent information read/write mechanism 21 on the RFID tag attached to the reagent container 12, the initial value of the placing elapsed time during the temperature abnormality period in the replenishment reagent depository 20 is updated.

As mentioned before the reagent information written on the RFID attached to the reagent container in the present invention, a detailed description is next given of reagent information written on the RFID on the discharge route from the analyzing unit 10.

The control computer 38 stores reagent information to be managed on the automatic analysis during a period until the reagent container 12 is discharged into the storing portion 39b installed in the reagent discharge-storage mechanism 26 after it was transferred into the reagent depository 28 or 29. Such reagent information includes the elapsed time of the reagent container placed in the reagent depository 28 or 29 and its permissible limit value, the temperature in the reagent depository and its permissible limit value, the cap-opening history of the reagent container 12, the combination of the reagent containers, the fluid volume of the reagent container, and the number of analysis. The reagent information is hereinafter described individually.

The control computer 38, as the reagent information written on the RFID, the placing elapsed time until the reagent container 12 is discharged after it was transferred into the reagent depository 28 or 29. It is desirable that the measurement of the placing elapsed time be started from a point of time when the reagent container 12 is transferred into the reagent depository 28 or 29.

The automatic analyzer includes a temperature sensor in the reagent depository 28 or 29. The control computer 38 stores, as another piece of reagent information written on the RFID, the temperature of the reagent depository 28 or 29. Temperature is constantly measured in the state where the automatic analyzer operates.

Similarly to the replenishment reagent depository 20, the placing elapsed time and the temperature for each of the reagent depositories 28 and 29 are each assigned a permissible limit value. The time when each of them exceeds the associated permissible limit value is stored in the control computer 38.

If the RFID read information on the reagent container includes a previous value, accumulation (the sum of the previous value and a current value) of the placing elapsed time is stored in the control computer 38. The previous value includes not only an initial value having no write history but also a value written by the reagent information read/write mechanism 35. If the placing elapsed time is written on the RFID tag, the initial value of the placing elapsed time is updated.

The control computer 38 stores, as the reagent information relating to the temperature permissible limit value, the placing elapsed time during a period of temperature abnormality in the range of from a starting point, i.e., the time when the temperature of the reagent depository 28 or 29 exceeds the permissible limit value to the time when the temperature becomes a value less than the permissible limit value. The control computer also stores the accumulation (the sum of the previous value and the concurrent value) of the placing elapsed time during the temperature abnormality period.

If the RFID read information on the reagent container includes the previous value of the placing elapsed time during the temperature abnormality period, the accumulation (the sum of the previous value and the current value) of the placing elapsed time during the temperature abnormality period is written. If not only an initial value having no write history in the previous value but also the placing elapsed time is written on the RFID tag, the initial value of the placing elapsed time during the temperature abnormality period in the reagent depository A28 or B29 is updated.

The automatic analyzer includes fluid volume detecting means installed on the reagent dispensing mechanism. The fluid volume detecting means is of a capacitance type or other types and detects the fluid volume of the reagent container 12, as another piece of reagent information written on the RFID, transferred into the reagent depository 28 or 29. Such fluid volume is stored in the control computer 38.

The automatic analyzer includes in the control computer the means for calculating how many analyses are executable in the appropriate reagent container. The number of analysis executable is stored as reagent information relating to the fluid volume in the control computer 38.

The reagent information written on the RFID in the embodiment of the present invention includes not only the fluid volume of the reagent container and the number of analysis which are reagent information continuously usable in another automatic analyzer but also the cap-opening history of the reagent container and the combination of the reagent containers which are described in the above-mentioned embodiment.

These pieces of the reagent information are written by the reagent information read/write mechanism B35 on the RFID tag attached to the reagent container 12 immediately after the reagent container 12 has been discharged from the reagent depository A28 or B29 to the storing portion 39b installed in the reagent discharge-storage mechanism 26.

EXPLANATION OF REFERENCE NUMERALS

10 Analyzing unit
11 Buffer unit
12 Reagent container
20 Replenishment reagent depository
21 Reagent information read/write mechanism A
22 Reagent transfer mechanism
23 Reagent cap opening mechanism
24 Reagent replenishment mechanism
25 Reagent discharge mechanism
26 Reagent discharge-storage mechanism
27 Reagent transfer mechanism
28 Reagent depository A
29 Reagent depository B
30 Reagent slot A
31 Reagent slot B
32 Reagent turning mechanism
33 Reaction mechanism
34 Reagent cap discard box
35 Reagent information read/write mechanism B
36 Information recording medium
37 Reagent dispensing mechanism
38 Control computer
39a Storing portion for discharged reagent container
39b Storing portion for discharged reagent containers 40 Reagent cap detecting mechanism
41 Elapsed time in the storing place
42 Temperature

The invention claimed is:
1. An automatic analyzer having an analyzing unit and a buffer unit, the automatic analyzer comprising:
a reagent container containing a reagent, the reagent container being provided with an information recording medium which records reagent information;
a reagent dispensing mechanism for dispensing the reagent received from the reagent container;
a reaction container adapted to mix the reagent dispensed by the reagent dispensing mechanism with a sample;
a reagent information read/write mechanism configured to write the reagent information on the information recording medium and read the reagent information on the information recording medium;
a first reagent depository in the analyzing unit which stores a plurality of the reagent containers;
a second replenishment reagent depository in the buffer unit which stores a replacement reagent container and which does not have a cold storage function therein;
a reagent transfer mechanism which transfers the reagent container from the second replenishment reagent depository to the first reagent depository; and
a reagent discharge mechanism having a storing portion which stores the reagent container discharged from the second replenishment reagent depository,
wherein the second replenishment reagent depository and at least one of the first reagent depository and the reagent transfer mechanism includes the reagent information read/write mechanism,
wherein the automatic analyzer includes a computer, coupled to the reagent information read/write mechanism and the reagent transfer mechanism, programmed to control the reagent information read/write mechanism to write the reagent information on the information recording medium immediately before the reagent container is transferred from the second replenishment reagent depository to the first reagent depository or immediately before the reagent container is discharged from the second reagent depository to the storing portion,
wherein the reagent information read/write mechanism included in the second replenishment reagent depository reads the reagent information from the information recording medium of the reagent container and the computer is programmed to store the reagent information and store a first time of when the reagent information is stored,
wherein the computer is programmed to control the reagent transfer mechanism to transfer the reagent container from the second replenishment reagent depository to the first reagent depository and store a second time of when the transfer begins,
wherein the computer is programmed to measure an elapsed time from the first time to the second time and store the measured elapsed time, and
wherein the elapsed time is reagent information written on the information recording medium by the reagent information read/write mechanism included in one of the second replenishment reagent depository, the first reagent depository, and the reagent transfer mechanism immediately before the reagent container is transferred from the second replenishment reagent depository to the first reagent depository.

2. The automatic analyzer according to claim 1,
wherein the computer is programmed to control the second replenishment reagent depository to discharge the reagent container to the reagent discharge mechanism and store a third time of when the reagent container is discharged
wherein the elapsed time is measured from the first time to the third time and the elapsed time is written by the reagent information read/write mechanism included in the second replenishment reagent depository immediately before the reagent container is discharged from the second replenishment reagent depository to the storing portion.

3. The automatic analyzer according to claim 1,
wherein the reagent information read/write mechanism reads the elapsed time written on the information recording medium, and
wherein the computer is programmed to control the reagent information read/write mechanism to write an updated elapsed time, which is a fourth time that has elapsed since the first time on the information recording medium.

4. The automatic analyzer according to claim 1,
wherein the computer stores a permissible limit value of the elapsed time in the second replenishment reagent depository, and
wherein the computer is programmed to control such the reagent information read/write mechanism to write information that the elapsed time exceeds the permissible limit value on the information recording medium immediately before the reagent container is transferred from the second replenishment reagent depository to the first reagent depository or immediately before the reagent container is discharged from the second replenishment reagent depository to the storing portion.

5. The automatic analyzer according to claim 1, further comprising:
a temperature sensor which measures a temperature of the second replenishment reagent depository,
wherein the computer stores a permissible limit value for the temperature measured by the temperature sensor, and
wherein the computer is programmed to control such that a time period during which the temperature exceeds the permissible limit value is written on the information recording medium immediately before the reagent container is transferred from the second replenishment reagent depository to the first reagent depository or immediately before the reagent container is discharged from the second replenishment reagent depository to the storing portion.

6. The automatic analyzer according to claim 1,
wherein the information recording medium is an RFID.

7. An automatic analyzer having an analyzing unit and a buffer unit, the automatic analyzer comprising:
a reagent container containing a reagent, the reagent container being provided with an information recording medium which records reagent information;
a reagent dispensing mechanism for dispensing the reagent received from the reagent container;
a reaction container adapted to mix the reagent dispensed by the reagent dispensing mechanism with a sample;
a reagent information read/write mechanism configured to write the reagent information on the information recording medium and read the reagent information on the information recording medium;

a first reagent depository in the analyzing unit which stores a plurality of the reagent containers;
a second replenishment reagent depository in the buffer unit which stores a replacement reagent container;
a reagent transfer mechanism which transfers the reagent container from the second reagent depository to the first reagent depository; and
a reagent discharge mechanism having a storing portion which stores the reagent container discharged from the second replenishment reagent depository,
wherein the second replenishment reagent depository and at least one of the first reagent depository and the reagent transfer mechanism includes the reagent information read/write mechanism,
wherein the automatic analyzer includes a computer, coupled to the reagent information read/write mechanism, programmed to control the reagent information read/write mechanism to write the reagent information on the information recording medium immediately before the reagent container is transferred from the second replenishment reagent depository to the first reagent depository or immediately before the reagent container is discharged from the second replenishment reagent depository to the storing portion,
wherein the reagent information read/write mechanism included in the second replenishment reagent depository reads the reagent information from the information recording medium of the reagent container and the computer is programmed to store the reagent information and store a first time of when the reagent information is stored,
wherein the computer is programmed to control the reagent transfer mechanism to transfer the reagent container from the second replenishment reagent depository to the first reagent depository and store a second time of when the transfer begins,
wherein the computer is programmed to measure an elapsed time from the first time to the second time and store the measured elapsed time, and
wherein the elapsed time is reagent information written on the information recording medium by the reagent information read/write mechanism included in one of the second replenishment reagent depository, the first reagent depository, and the reagent transfer mechanism immediately before the reagent container is transferred from the second replenishment reagent depository to the first reagent depository.

8. The automatic analyzer according to claim 7,
wherein the computer is programmed to control the second replenishment reagent depository to discharge the reagent container to the reagent discharge mechanism and store a third time of when the reagent container is discharged, and
wherein the elapsed time is measured from the first time to the third time and the elapsed time is written by the reagent information read/write mechanism included in the second replenishment reagent depository immediately before the reagent container is discharged from the second reagent depository to the storing portion.

9. The automatic analyzer according to claim 7,
wherein the reagent information read/write mechanism reads the elapsed time written on the information recording medium, and
wherein the computer is programmed to control the reagent information read/write mechanism to write an updated elapsed time, which is a fourth time that has elapsed since the first time on the information recording medium.

10. The automatic analyzer according to claim 7,
wherein the computer stores a permissible limit value of the elapsed time in the second replenishment reagent depository, and
wherein the computer is programmed to control the reagent information read/write mechanism to write information that the elapsed time exceeds the permissible limit value on the information recording medium immediately before the reagent container is transferred from the second replenishment reagent depository to the first reagent depository or immediately before the reagent container is discharged from the second replenishment reagent depository to the storing portion.

11. The automatic analyzer according to claim 7, further comprising:
a temperature sensor which measures a temperature of the second replenishment reagent depository,
wherein the computer stores a permissible limit value for the temperature measured by the temperature sensor, and
wherein the computer is programmed to control such that a time period during which the temperature exceeds the permissible limit value is written on the information recording medium immediately before the reagent container is transferred from the second replenishment reagent depository to the first reagent depository or immediately before the reagent container is discharged from the second replenishment reagent depository to the storing portion.

12. The automatic analyzer according to claim 7, wherein the information recording medium is an RFID.

* * * * *